(12) United States Patent
Krebs (10) Patent No.: US 9,657,094 B2
(45) Date of Patent: May 23, 2017

(54) BIODEGRADABLE POLYMERS FOR DELIVERY OF THERAPEUTIC AGENTS

(71) Applicant: COLORADO SCHOOL OF MINES, Golden, CO (US)

(72) Inventor: Melissa D. Krebs, Englewood, CO (US)

(73) Assignee: Colorado School of Mines, Golden, CO (US)

(*) Notice: Subject to any disclaimer, the term of this patent is extended or adjusted under 35 U.S.C. 154(b) by 0 days.

(21) Appl. No.: 14/312,772

(22) Filed: Jun. 24, 2014

(65) Prior Publication Data

US 2014/0377366 A1    Dec. 25, 2014

Related U.S. Application Data

(60) Provisional application No. 61/838,797, filed on Jun. 24, 2013.

(51) Int. Cl.
| | |
|---|---|
| *A61K 9/16* | (2006.01) |
| *C07K 16/22* | (2006.01) |
| *A61K 47/36* | (2006.01) |
| *A61K 9/00* | (2006.01) |
| *A61K 9/06* | (2006.01) |

(52) U.S. Cl.
CPC ........... *C07K 16/22* (2013.01); *A61K 9/0019* (2013.01); *A61K 9/06* (2013.01); *A61K 9/1647* (2013.01); *A61K 9/1652* (2013.01); *A61K 47/36* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 2004/0175381 A1* | 9/2004 | Winsor-Hines | C07K 16/2812 424/144.1 |
| 2005/0074497 A1* | 4/2005 | Schultz | A61K 9/0048 424/486 |
| 2008/0031873 A1* | 2/2008 | Fasick et al. | 424/133.1 |
| 2008/0085295 A1* | 4/2008 | Melvik et al. | 424/423 |
| 2008/0138416 A1* | 6/2008 | Rauh | A61K 38/06 424/488 |
| 2009/0061010 A1* | 3/2009 | Zale et al. | 424/501 |
| 2010/0029789 A1* | 2/2010 | Chen | A61L 27/26 514/777 |

OTHER PUBLICATIONS

J Ma, J Samuel, GS Kwon, AA Noujaim, R Madiyalakan. "Induction of anti-idiotypic humoral and cellular immune responses by a murine monoclonal antibody recognizing the ovarian carcinoma antigen CA125 encapsulated in biodegradable microspheres." Cancer Immunology and Immunotherapy, vol. 47, 1998, pp. 13-20.*

(Continued)

*Primary Examiner* — Isaac Shomer
(74) *Attorney, Agent, or Firm* — Dorsey & Whitney LLP (57) ABSTRACT

Methods, processes, systems, and compositions for treating disease are disclosed. In some cases, the present disclosure provides for delivery of therapeutic agents, in an active form, to a localized area, over an extended period of time. In one embodiment, the disclosed composition may comprise a therapeutic agent and a biodegradable polymer and/or a biodegradable polymer microsphere.

13 Claims, 6 Drawing Sheets

(56) References Cited

OTHER PUBLICATIONS

RR Torelli-Souza, LA Cavalcante Bastos, HGL Nunes, CA Camara, RVS Amorim. "Sustained Release of an Antitumoral Drug from Alginate-Chitosan Hydrogel Beads and Its Potential Use as Colonic Drug Delivery." Journal of Applied Polymer Science, vol. 126, 2012, pp. E408-E417.*

RS Ashton, A Banerjee, S Punyani, DV Schaffer, RS Kane. "Scaffolds based on degradable alginate hydrogels and poly(lactide-co-glycolide) microspheres for stem cell culture." Biomaterials, vol. 28, 2007, pp. 5518-5525.*

YK Joung, JH Choi, KM Park, KD Park. "PLGA microparticle-embedded thermosensitive hydrogels for sustained release of hydrophobic drugs." Biomedical Materials, vol. 2, 2007, pp. 269-273.*

C-H Zheng, J-Q Gao, Y-P Zhang, W-Q Liang. "A protein delivery system: biodegradable alginate-chitosan-poly(lactic-co-glycolic acid) composite microspheres." Biochemical and Biophysical Research Communications, vol. 323, 2004, pp. 1321-1327.*

Y Xu, C Zhan, L Fan, L Wang, H Zheng. "Preparation of dual crosslinked alginate-chitosan blend gel beads and in vitro controlled release in oral site-specific drug delivery system." International Journal of Pharmaceutics, vol. 336, 2007, pp. 329-337.*

Y Xu, C Zhang, L Fan, L Wang, H Zheng. "Preparation of dual crosslinked alginate-chitosan blend gel beads and in vitro controlled release in oral site-specific drug delivery system." International Journal of Pharmaceutics, vol. 336, 2007, pp. 329-337.*

J Lee, KY Lee. "Injectable Microsphere/Hydrogel Combination Systems for Localized Protein Delivery." Macromolecular Bioscience, vol. 9, 2009, pp. 671-676.*

Carter, Paul J. "Potent antibody therapeutics by design", Nature Reviews Immunology 6, 343-357 (May 2006).

Hollinger, Philipp et al., "Engineered antibody fragments and the rise of single domains", Nature Biotechnology 23, 1126-1136 (2005), Published online: Sep. 7, 2005.

Krebs, Melissa D. et al., "Detection of Biological and Chemical Agents Using Differential Mobility Spectrometry (DMS) Technology", Sensors Journal, IEEE, vol. 5, No. 4, pp. 696,703, Aug. 2005.

* cited by examiner

BIODEGRADABLE POLYMERS FOR DELIVERY OF THERAPEUTIC AGENTS

CROSS REFERENCE TO RELATED APPLICATIONS

This application claims benefit of priority pursuant to 35 U.S.C. §119(e) of U.S. provisional patent application No. 61/838,797 filed 24 Jun. 2013, which is hereby incorporated herein by reference in its entirety.

FIELD

The disclosed processes, methods, and systems are directed to delivery systems for use in the administration of therapeutic antibodies.

BACKGROUND

Certain diseases are more difficult to treat than others. For example, some cancerous tumors may occur in remote or sensitive parts of the body. Removal of these types of tumor may require extensive, invasive, and/or delicate surgeries. If all of the tumor is not removed, repeated surgeries may be required. Repeated surgery in some parts of the body dramatically increases the risk of complications. One such area is within the central nervous system (the CNS), which is protected by the blood-brain barrier.

CNS cancer is deadly, and especially difficult to treat. Approximately 23,000 new cases of brain (and other nervous system) cancer were diagnosed this past year in the U.S., and about 14,000 people die annually as a result of the disease. 36% of the diagnosed cases are gliomas and half of these are glioblastoma, an extremely aggressive cancer with poor patient prognosis.

Current therapies, such as surgery, radiation, and chemotherapy, allow for a median survival of less than 14 months. At present, the standard of care includes surgical resection of the tumor and treatment with chemotherapy or radiation. In many cases, there may be no clear division between the tumor and normal brain tissue. Thus, it is not possible, usually, to remove all the cancerous cells. There is currently no cure for gliomas and no current treatments prevent its recurrence. Glioma's resistance to therapy is due, at least in part, to the fact that chemotherapeutic drugs, administered systemically, must traverse the blood-brain barrier (BBB).

In order to avoid the need to traverse the BBB, an implantable drug delivery system has been developed. That therapy, the Gliadel® wafer, is FDA-approved for the treatment of malignant glioblastomas. Gliadel therapy involves the placement of solid, biodegradable, polymeric wafers into the tumor resection cavity. The Gliadel wafer then slowly releases a chemotherapeutic drug, carmustine (a small molecule drug), which diffuses out of the wafer and into the surrounding tissues. Over 20,000 patients have had this treatment since it was launched in 1997; unfortunately it is associated with little improvement in survival. Poor efficacy of Gliadel is likely due to the cancer cells' abilities to overcome the effect of this therapy via expression of DNA repair enzymes.

Drugs directed to specific molecular targets, rather than nonspecific chemotherapeutic drugs such as carmustine may aid in treating individual cancers. For example, glioblastomas are highly angiogenic, meaning they encourage epithelial cells to form blood vessels that then help to feed the cancer cells. To do this, gliomas produce large amounts of a protein called Vascular Endothelial Growth Factor, or VEGF, that stimulates angiogenesis. Bevacizumab (Avastin), an anti-VEGF antibody targets angiogenesis by binding VEGF. Bevacizumab is FDA-approved for treating glioblastoma. Results of this therapy are promising, but the prognosis remains poor. Specifically, phase I and II clinical trials involving intravenous administration of Bevacizumab show that some patients have responded sufficiently to extend life expectancy several months. Poor prognosis likely stems from the need for repeated injections of antibody, due to rapid clearance of the antibody from the body. Additionally, antibodies delivered intravenously must, like other systemically delivered therapies, cross the blood-brain barrier, which is not likely to result in high concentration within the CNS.

While antibody-based treatment of tumors shows great clinical promise, the use of therapeutic antibodies for brain and other CNS cancers remains a challenge. This is because systemic (intravenous) delivery of antibodies is difficult since the therapeutic antibodies must cross the blood-brain barrier, which normally excludes large molecules. Thus, in order to treat CNS diseases by systemic administration of therapeutic agents, repeated injections, usually, in large doses are required. In the case of therapeutic antibodies, efficacy is further hindered by rapid clearance from the body.

What is needed is an approach that can deliver therapeutic agents to a localized area, for example within the brain or CNS, wherein delivery occurs over an extended period of time.

SUMMARY

Disclosed herein are compositions and methods for use in delivering therapeutic agents to a localized area, wherein delivery can occur over an extended period of time. Localized delivery of therapeutic agents may enhance efficacy by increasing local concentrations of the therapeutic agent, and prolonging exposure of the treatment site to the therapeutic agent. Moreover, localized delivery may be useful in treating diseases in locations that are difficult to access, for example within the CNS. In some cases, the disclosed compositions and methods may aid in delivery of therapeutic antibodies to a site where a brain tumor has been removed. This method may lessen the need to repeatedly access the resection site and/or systemically administer therapeutic agents, such as antibodies or chemotherapy.

The presently disclosed compositions and methods are also useful in maintaining activity of the therapeutic agent. For example the compositions disclosed herein may aid in protecting against degradation of the therapeutic agent. This may be useful where the therapeutic agent is susceptible to metabolism, degradation, and/or denaturation. For example, where the therapeutic agent is a biopharmaceutical, such as a compound containing nucleic acid or amino acid.

One embodiment of the presently disclosed compositions and methods may be useful in the treatment of brain tumors, for example, glioma. Glioblastoma, a subtype of glioma, is an extremely aggressive brain cancer with poor patient prognosis. The median survival time for patients with glioblastoma is less than 14 months. The standard of care in glioblastoma first includes surgical resection of the tumor. Because there is no clear division between the glioblastoma tumor and the patient's healthy brain tissue, it is often difficult to remove the cancerous cells completely. Thus, surgery is usually followed by chemotherapy and/or radiation therapy to try and kill the remaining tumor cells. As the survival time suggests, this is rarely successful, and there is no treatment for recurrence of glioblastoma.

The presently disclosed compositions and methods offer promising alternative approaches to treating glioblastoma as well as other diseases and conditions. For example, rather than relying on repeated intravenous injections of anti-VEGF to treat glioblastoma, the present disclosure would allow placement of an antibody-laden biodegradable hydrogel system into the tumor resection cavity. The antibody-laden biodegradable hydrogel would then release anti-VEGF to the periphery of the resection site in a localized manner, and at steady rate over a sustained period of time. Use of the disclosed biopolymer system would also aid in protecting the therapeutic antibody, allowing it to maintain its bioactivity.

Treatment methods disclosed herein may comprise resecting a tumor, for example a glioma tumor, followed by placing the disclosed composition comprising a biodegradable polymer or biodegradable gel, a therapeutic agent, for example anti-VEGF antibodies, into the resection site, with the sustained and steady delivery of the therapeutic agent, for example an anti-angiogenic antibody to the resected area. The therapeutic antibody aids in inhibiting growth of any remaining tumor cells while it is released from the biodegradable polymer over time. In some cases, release of the antibody from the biopolymer may be aided by degradation of the biopolymer and/or diffusion from the biodegradable polymer or biodegradable gel.

The present disclosure is directed to compositions and methods to provide controlled delivery systems for therapeutic agents that can enhance the delivery of various agents in a localized treatment site. In some embodiments the disclosed compositions and methods may be used to treat localized cancers and/or aid in tissue regeneration. In tissue regeneration applications, the disclosed compositions and methods may be useful in inhibition of proteins that impede healing or regeneration.

The present disclosure is directed to compositions and methods of treating using compositions of injectable, antibody-laden biodegradable hydrogel, for delivery of therapeutic antibody to a localized site, wherein release of active therapeutic antibody is stable over a sustained period of time. In some embodiments, the biodegradable polymer may be solid or semi-solid. In one embodiment, the biodegradable polymer/antibody composition may be useful in the treatment of glioma cancer. Such compositions and methods may help reduce costs, reduce unwanted side effects that can occur in systemic intravenous delivery, and provide a stronger patient response to the therapy, as the affected area will be continually exposed to bioactive antibody as it is released from the biopolymer system.

In many embodiments, the disclosed compositions and methods may aid in protecting the therapeutic agent over an extended period of time. For example, where the agent is an antibody, such as anti-VEGF, the disclosed composition may allow the antibody to maintain bioactivity. In this embodiment, the composition could be used to treat glioma after resection of the glioma. In this embodiment, the tumor is resected and the composition, comprising the therapeutic antibody, is injected into the resection site, allowing sustained delivery of active anti-angiogenic antibody to the area to aid in inhibiting the growth of remaining tumor cells. In many embodiments, release may be aided by diffusion and degradation of the biodegradable gel.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed description is to be regarded as illustrative in nature and not restrictive.

BRIEF DESCRIPTION OF THE DRAWINGS

FIG. 2(a) shows DNA nanoparticles released from alginate hydrogels, FIG. 2(b) shows siRNA released from photo-crosslinkable alginate and collagen hydrogels, and FIG. 2(c) shows BMP-2 protein released from alginate and heparin-alginate hydrogels.

DETAILED DESCRIPTION

Described herein are compositions for delivery of a therapeutic agent, the composition comprising a therapeutic agent, and a biodegradable polymer, biodegradable scaffold, or biodegradable gel. In some embodiments the therapeutic agent is comprised of amino acids, peptide, or protein, for example an antibody. In some embodiments the therapeutic agent is encapsulated, for example in a microsphere of poly(lactic-co-glycolic acid, of varying ratios and molecular weights). The biodegradable polymer can be a polymer gel, for example a hydrogel comprising alginate, chitin, or other suitable polymer. The molecular weight of the polymer may be from about 50 kDa to about 200 kDa or greater. In some embodiments, the composition may further include a chemotherapeutic agent, for example carmustine.

Also described herein are methods of delivering a therapeutic agent to a treatment site comprising combining the therapeutic agent and a biodegradable polymer to create a therapeutic composition, placing the therapeutic composition at a treatment site; and thereby, delivering the therapeutic agent. In some embodiments, the treatment site may be a location of a resected tumor, for example a tumor or glioma growing inside the blood-brain barrier. In some cases, for example where the polymer is a gel, the therapeutic agent may be placed at the treatment site by injection, for example via a syringe. In some cases, for example where the polymer is a semi-solid or solid, the therapeutic agent may be placed at the treatment site using a process that may or may not include injection. In some embodiments, the method is used to deliver a therapeutic agent with the property of stimulating tissue growth or of inhibiting angiogenesis.

Recent advancements in cancer therapy involve finding molecular targets specific to individual cancers. One target for tumors is the process of angiogenesis, which creates new blood vessels to feed growing tumors. Vascular endothelial growth factor (VEGF) is a signal protein involved in angiogenesis, and the target of anti-cancer therapies. Specifically, antibodies that bind VEGF (anti-VEGF) have been used to prevent a tumor from creating new blood vessels. Thus, effectively starving the tumor and restricting its growth.

Antibody-based treatment of many different types of tumors shows clinical promise. However the use of these therapeutic antibodies for brain and other nervous system cancers remains a challenge. This is because complex molecules, have difficulty entering the central nervous system, for examples when antibodies are administered systemically (for example, intravenously).

The central nervous system is protected by the blood-brain barrier (BBB), which acts to separate the blood from the cerebrospinal fluid surrounding the brain and spinal cord. While the blood-brain barrier is effective at protecting the CNS against bacterial and viral infection, it also has the effect of hindering the treatment of CNS disease because therapeutic agents may be excluded. Some small molecules and oxygen can diffuse across the blood-brain barrier, but larger molecules, for example antibodies, and some smaller molecules are excluded. The difficulty most large molecules have in traversing the BBB means that intravenously-delivered antibodies have difficulty in being effective against brain tumors. Another problem with the administration of antibodies systemic for the treatment of CNS tumors is due to the rapid clearance of therapeutic antibodies from the blood stream. Together these two barriers, the BBB and rapid clearance, means that patients must receive repeated injections of therapeutic antibodies in large doses. In many cases, the expense of therapeutic antibodies results in very costly treatment regimes.

The FDA has approved treatment of CNS cancer with a therapeutic antibody. Specifically, anti-VEGF antibodies (bevacizumab or Avastin) have been approved by the FDA for treatment of glioblastomas. These antibodies may be effective against glioblastoma because these tumors produce VEGF and are highly angiogenic. The data is preliminary, and in phase I and II clinical trials, some glioblastoma patients have shown response to anti-VEGF. While this response has been reported to last several months, the dosing and treatment schedule have not been optimized. As a result the prognosis remains poor.

Other avenues for enhancing the efficacy of therapeutic antibody treatment of CNS disease have been attempted. One possible solution is to injection the antibody directly into the brain. This type of delivery has been attempted with IgG. However, after injection, the IgG levels drop off considerably within the first few days. A second solution is to implant the antibody within the brain. In these studies, IgG is implanted directly into the brain within a carrier of non-degrading polymer. Results from these studies show a higher IgG level within the brain for 28 days following implantation. However, because the carrier is non-degradable, a second surgery is required to remove the implant.

The presently disclosed methods and compositions are directed to delivering therapeutic agent to a treatment site, wherein the agent is delivered over an extended period of time. In some cases, this sustained and stable release of a therapeutic agent may offer an effective strategy for delivery of therapeutic antibodies to CNS tumor sites. The disclosed methods and compositions may aid in improving patient response, minimizing side effects, and reducing the overall treatment cost. In one embodiment, the disclosed methods and compositions may deliver anti-angiogenic antibodies, in a localized manner, to gliomas, which is a highly angiogenic type of brain tumor. In some cases, the present disclosure provides for this delivery without the need for repeated applications, or injections of the therapeutic agent, and without the need for repeated access to the treatment site. In many cases, the disclosed composition is a biodegradable gel that releases the therapeutic over a period of time.

Use of the disclosed biodegradable polymer may aid in treating a site that is not easily accessible by other methods, for example treatment sites accessible only by invasive surgery, and/or protected by a barrier, such as the blood-brain barrier. The blood-brain barrier is normally difficult for large molecules to traverse.

The presently disclosed compositions and methods can be used at treatment sites, for example the site of a tumor, that are difficult to access. In one embodiment the presently disclosed compositions can be used to treat brain tumors and other CNS diseases. Use of the disclosed compositions and methods may help to obviate or lessen the need for repeated administrations of intravenous therapeutic agents, for example, a therapeutic antibody, which would be required to traverse the blood brain barrier. In the case of CNS treatment, the disclosed compositions and methods, would allow sustained delivery of a therapeutic antibody directly to a treatment site, without the need for repeated and/or continuous breach of the blood brain barrier by surgical or other physical methods. For example, in the case of anti-VEGF treatment of glioblastoma, the present disclosure would allow placement of an antibody-laden biodegradable hydrogel system into the tumor resection cavity. The antibody-laden biodegradable hydrogel would allow release of anti-VEGF to the periphery of the resected tumor site in a localized manner with stable release rate over a sustained period of time. In this embodiment, antibody would be released by diffusion out of the biopolymer, or as the biopolymer is degraded. In some embodiments, the disclosed composition may further comprise a particle, for example a nano- or microparticle. The disclosed biopolymer system would also aid in protecting the therapeutic agent, allowing the therapeutic agent to maintain its bioactivity during the prolonged delivery process.

The disclosed composition may be used to deliver a therapeutic agent to a treatment site that is in need of tissue regeneration or tissue healing. In these cases the therapeutic agent may be a compound that enhances, encourages, or protects growth or regeneration of cells, tissues, organs, vessels, systems, or other structures.

Methods disclosed herein may comprise administering the disclosed composition to a treatment site. Treatment sites may include cancerous tissue, for example tumor sites (before or after resection), and sites of tissue damage, for example sites in need of regeneration or healing. In some cases, treatment methods disclosed herein may comprise resecting a tumor, for example a glioma tumor, followed by placing the disclosed composition with the site of resection to allow for controlled delivery of the therapeutic agent. In some embodiments the disclosed compositions and methods may comprise resecting a glioma tumor followed by placing the claimed composition comprising a biodegradable gel and a therapeutic agent (for example a therapeutic antibody) into the resection site. Where the therapeutic antibody is an anti-angiogenic antibody, growth of remaining tumor cells may be inhibited because angiogenesis is inhibited, or significantly reduced, while the antibody is released from the hydrogel in a sustained manner. In some cases, release of the therapeutic antibody from the biodegradable polymer may be aided by degradation of the polymer.

The disclosed biodegradable polymer may aid in release of a therapeutic agent at a treatment site. In some cases a biodegradable gel may be used, for example a biodegradable hydrogel that may aid in release of a therapeutic antibody at the tumor resection site. In some embodiments, the release can be in a localized manner with a stable release rate over a sustained period of time. In one embodiment, a composition comprising a hydrogel and a therapeutic can be introduced into a resection site, and delivery of the antibody can aid in inhibiting growth of remaining tumor cells. In another embodiment, the antibody can be combined with a chemotherapeutic drug within the hydrogel for dual drug delivery at a tumor or resection site. For example, a first therapeutic agent may be an antibody that inhibits angiogenesis, and a second therapeutic agent may be a chemotherapeutic agent that inhibits the growth of cancer cells.

Use of the described biodegradable polymer may help reduce costs and occurrence of unwanted side effects, for example those associated with systemic, intravenous delivery, and/or repeated administration of therapeutic agents. Localized, stable release of the therapeutic agent from a biodegradable polymer may also help provide a stronger patient response to the therapy because the delivery is sustained and the local concentration of the therapeutic agent is high. Use of the described polymer may increase efficacy as the treatment area will be continually exposed to therapeutic agent as it is released from the biodegradable polymer.

Biodegradable Polymer

Biodegradable polymer, as disclosed herein may refer to a solid, a semi-solid, a scaffold, or a gel comprising a degradable polymer. Biodegradable, as used herein, may refer to synthetic or naturally occurring molecules that can be broken down into non-toxic, harmless, or innocuous molecules or constituent parts. The process of breaking down a biodegradable molecule may be through cellular, enzymatic, and/or chemical means.

The molecular weight of a polymer in the biodegradable polymer may be from about 50 kDa to about 200 kDa. In some embodiments the molecular weight of the polymer may be greater than about 50 kDa, 60 kDa, 70 kDa, 80 kDa, 90 kDa, 100 kDa, 110 kDa, 120 kDa, 130 kDa, 140 kDa, 150 kDa, 160 kDa, 170 kDa, 180 kDa, 190 kDa, 200 kDa, 210 kDa, 220 kDa, 230 kDa, 240 kDa, 250 kDa, 300 kDa, 350 kDa, 400 kDa, 450 kDa, or 500 kDa and less than about 550 kDa, 500 kDa, 450 kDa, 400 kDa, 350 kDa, 300 kDa, 250 kDa, 240 kDa, 230 kDa, 220 kDa, 210 kDa, 200 kDa, 190 kDa, 180 kDa, 170 kDa, 160 kDa, 150 kDa, 140 kDa, 130 kDa, 120 kDa, 110 kDa, 100 kDa, 90 kDa, 80 kDa, 70 kDa, or 60 kDa.

The biodegradable polymer may be a polymer that is natural, synthetic, or a combination thereof. Exemplary polymers include alginate, chitosan, hyaluronic acid, collagen, GAG (glycosaminoglycan), chondroitan sulfate, poly(ethylene glycol) (PEG), gelatin, poly(lactic-co-glycolic acid) (PLGA), polyesters, and combinations thereof, such as collagen/GAG scaffolds, alginate/chitosan composites, and alginate/PEI (polyethylenimine) composites. In some cases, alginate may be obtained from seaweed and may consists of 1,4-linked β-D-mannuronic acid and α-L-guluronic acid. In many embodiments, alginate may reduce biofouling of the composition.

In some cases, the ratio of polymer subunits may be varied to control for various characteristics of the gel, for example rate of degradation, viscosity, etc. In some cases, where the polymer includes PLGA, the ratio of lactic acid to glycolic acid may be varied, for example the percent by weight of lactic acid may be greater than about 50%, 55%, 60%, 65%, 70%, 75%, 80%, 85%, 90%, or 95%, and less than about 100%, 95%, 90%, 85%, 80%, 75%, 70%, 65%, 60%, 55%, 50%, or 45%, with the remainder comprising glycolic acid to give a total of 100%.

In some embodiments, the biodegradable polymer may be a solid biopolymer scaffold, a biodegradable gel, or a biodegradable hydrogel. A hydrogel may refer to gel comprising a network of one or more hydrophilic polymer chains, such as the polymers listed above. Hydrogels may be absorbent and may comprise greater than about 90% water by weight. In some embodiments, the hydrogel may be greater than 91% water, 92% water, 93% water, 94% water, 95% water, 96% water, 97% water, 98% water, or 99% water and less than about 100% water, 99% water, 98% water, 97% water, 96% water, 95% water, 94% water, 93% water, 92% water, or 91% water.

The biodegradable gel may be cross-linked. In some embodiments the cross-linking method may be accomplished by ionic-, covalent-, photo-crosslinking, or a combination thereof. In some cases where alginate is the polymer, the carboxylic acid groups on the guluronic acid units can be ionically crosslinked with divalent cations such as calcium.

Therapeutic Agents

The therapeutic agent disclosed herein may be any compound that may be administered to a mammal for preventative purposes or therapeutic purposes. In many cases, the therapeutic agent for use herein may be a biological compound. Biological compounds may include proteinaceous molecule such as an antibody, protein, or peptide. A biological compound may comprise one or more nucleic acids, amino acids, nucleic acid analogues, amino acid analogues, and/or combinations thereof. In one embodiment the therapeutic agent may be an antibody, for example an anti-angiogenesis antibody such as anti-VEGF.

In some embodiments, the nucleic acids, amino acids, nucleic acid analogues, and amino acid analogues may be synthetic or naturally occurring. In some cases the nucleic acids, amino acids, nucleic acid analogues, and amino acid analogues may be derivitized. Covalent modifications of therapeutic agents are included within the scope of therapeutic agents disclosed herein, and are generally, but not always, done post-translationally or post-synthesis. For example, several types of covalent modifications of the disclosed agent are introduced into the molecule by reacting specific amino acid or nucleic acid residues with an organic derivatizing agent that is capable of reacting with selected side chains, N- or C-terminal residues, or other chemical groups on the agent.

In some embodiments the therapeutic agent may aid in inhibiting the growth or migration of a cell, for example a cancer cell or blood vessel cell. In other embodiments, the therapeutic agent may aid in promoting growth, such as at the site of cell death, cell injury, or tissue damage/injury.

In some embodiments, the covalent modification of the compounds disclosed herein comprises the addition of one or more labels. The term "labeling group" means any detectable label. In some embodiments, the labeling group is coupled to the agent via spacer arms of various lengths to reduce potential steric hindrance. In other embodiments, the labeling group may be a second agent within the compound. Various methods for labeling proteins, nucleic acids, and other compounds are known in the art and may be used in generating immunoglobulins disclosed herein. In general, labels fall into a variety of classes, depending on the assay in which they are to be detected: a) isotopic labels, which may be radioactive or heavy isotopes; b) magnetic labels (e.g., magnetic particles); d) redox active moieties; d) optical dyes; enzymatic groups (e.g. horseradish peroxidase, β-galactosidase, luciferase, alkaline phosphatase); e) biotinylated groups; and f) predetermined polypeptide epitopes recognized by a secondary reporter (e.g., leucine zipper pair sequences, binding sites for secondary antibodies, metal binding domains, epitope tags, etc.). In some embodiments, the labeling group is coupled to the antibody via spacer arms of various lengths to reduce potential steric hindrance. Various methods for labeling proteins are known in the art and may be used in generating immunoglobulins disclosed herein. Specific labels include optical dyes, including, but not limited to, chromophores, phosphors and fluorophores, with the latter being specific in many instances. Fluorophores can be either "small molecule" fluores, or proteinaceous fluores. By "fluorescent label" is meant any molecule that may be detected via its inherent fluorescent properties.

The therapeutic agents disclosed herein may be administered concomitantly with one or more other therapeutic agents. The additional therapeutic agents may be used to improve the efficacy or safety of a first therapeutic agent. Also, the additional therapeutic regimes or agents may be used to treat the same disease or a comorbidity rather than to alter the action of the first therapeutic agent. For example, a first therapeutic agent disclosed herein may be administered to the patient along with chemotherapy, radiation therapy, or both chemotherapy and radiation therapy. The first therapeutic agent disclosed herein may be administered in combination with one or more other prophylactic or therapeutic agents, including but not limited to cytotoxic agents, chemotherapeutic agents, cytokines, growth inhibitory agents, anti-hormonal agents, kinase inhibitors, anti-angiogenic agents, cardioprotectants, immunostimulatory agents, immunosuppressive agents, agents that promote proliferation of hematological cells, angiogenesis inhibitors, protein tyrosine kinase (PTK) inhibitors, antibodies, or other therapeutic agents.

The skilled medical practitioner can determine empirically, or by considering the pharmacokinetics and modes of action of the agents, the appropriate dose or doses of each therapeutic agent.

In one embodiment, the therapeutic agents disclosed herein are administered with a chemotherapeutic agent. By "chemotherapeutic agent" as used herein is meant a chemical compound useful in the treatment of cancer. Examples of chemotherapeutic agents include but are not limited to alkylating agents such as thiotepa and cyclosphosphamide (CYTOXAN™); alkyl sulfonates such as busulfan, improsulfan and piposulfan; androgens such as calusterone, dromostanolone propionate, epitiostanol, mepitiostane, testolactone; anti-adrenals such as aminoglutethimide, mitotane, trilostane; anti-androgens such as flutamide, nilutamide, bicalutamide, leuprolide, and goserelin; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti estrogens including for example tamoxifen, raloxifene, aromatase inhibiting 4(5)-imidazoles, 4-hydroxtamoxifen, trioxifene, keoxifene, LY 117018, onapristone, and toremifene (Fareston); anti-metabolites such as methotrexate and 5-fluorouracil (5-FU); folic acid analogues such as denopterin, methotrexate, pteropterin, trimetrexate; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; folic acid replenisher such as frolinic acid; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; platinum analogs such as cisplatin and carboplatin; vinblastine; platinum; proteins such as arginine deiminase and asparaginase; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; taxanes, e.g. paclitaxel (TAXOL®, Bristol-Myers Squibb Oncology, Princeton, N.J.) and docetaxel (TAXOTERE®, Rhne-Poulenc Rorer, Antony, France); topoisomerase inhibitor RFS 2000; thymidylate synthase inhibitor (such as Tomudex); additional chemotherapeutics including aceglatone; aldophosphamide glycoside; aminolevulinic acid; amsacrine; bestrabucil; bisantrene; edatraxate; defofamine; demecolcine; diaziquone; difluoromethylornithine (DMFO); elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; chlorambucil; gemcitabine; 6-thioguanine; mercaptopurine; methotrexate; etoposide (VP-16); ifosfamide; mitomycin C; mitoxantrone; vincristine; vinorelbine; navelbine; novantrone; teniposide; daunomycin; aminopterin; xeloda; ibandronate; CPT-11; retinoic acid; esperamicins; capecitabine. Pharmaceutically acceptable salts, acids or derivatives of any of the above may also be used.

The therapeutic agent may be administered as a prodrug. By "prodrug" as used herein is meant a precursor or derivative form of a pharmaceutically active substance that is less cytotoxic compared to the parent drug and is capable of being activated or converted (enzymatically, spontaneously, or chemically) into the more active parent form. The prodrugs that may find use with compositions and methods disclosed herein include but are not limited to phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use with the antibodies disclosed herein include but are not limited to any of the aforementioned therapeutic agents.

A variety of other therapeutic agents may find use for administration with the antibodies disclosed herein. In one embodiment, the immunoglobulin is administered with an anti-angiogenic agent. By "anti-angiogenic agent" as used herein is meant a compound that blocks, or interferes to some degree, the development of blood vessels. The anti-angiogenic factor may, for instance, be a small molecule or a protein, for example an antibody, Fc fusion, or cytokine, that binds to a growth factor or growth factor receptor involved in promoting angiogenesis. In one embodiment, an anti-angiogenic factor may be an antibody that binds to Vascular Endothelial Growth Factor (VEGF). Other agents that inhibit signaling through VEGF may also be used, for example RNA-based therapeutics that reduce levels of VEGF or VEGF-R expression, VEGF-toxin fusions, Regeneron's VEGF-trap, and antibodies that bind VEGF-R. In an alternate embodiment, the antibody is administered with a therapeutic agent that induces or enhances adaptive immune response, for example an antibody that targets CTLA-4. Additional anti-angiogenesis agents include, but are not limited to, angiostatin (plasminogen fragment), antithrombin III, angiozyme, ABT-627, Bay 12-9566, benefin, bevacizumab, bisphosphonates, BMS-275291, cartilage-derived inhibitor (CM), CAI, CD59 complement fragment, CEP-7055, Col 3, combretastatin A-4, endostatin (collagen XVIII fragment), farnesyl transferase inhibitors, fibronectin fragment, gro-beta, halofuginone, heparinases, heparin hexasaccharide fragment, HMV833, human chorionic gonadotropin (hCG), IM-862, interferon alpha, interferon beta, interferon gamma, interferon inducible protein 10 (IP-10), interleukin-12, kringle 5 (plasminogen fragment), marimastat, metalloproteinase inhibitors (eg. TIMPs), 2-methodyestradiol, MMI 270 (CGS 27023A), plasminogen activator inhibitor (PAI), platelet factor-4 (PF4), prinomastat, prolactin 16 kDa fragment, proliferin-related protein (PRP), PTK 787/ZK 222594, retinoids, solimastat, squalamine, SS3304, SU5416, SU6668, SU11248, tetrahydrocortisol-S, tetrathiomolybdate, thalidomide, thrombospondin-1 (TSP-1), TNP-470, transforming growth factor beta (TGF-β), vasculostatin, vasostatin (calreticulin fragment), ZS6126, and ZD6474.

Antibodies/Immunoglobulins

By "antibody" herein is meant a protein consisting of one or more polypeptides substantially encoded by all or part of the recognized immunoglobulin genes. The recognized immunoglobulin genes, for example in humans, include the kappa (κ), lambda (λ), and heavy chain genetic loci, which together comprise the myriad variable region genes, and the constant region genes mu (μ), delta (δ), gamma (γ), sigma (σ), and alpha (α) which encode the IgM, IgD, IgG (IgG1, IgG2, IgG3, and IgG4), IgE, and IgA (IgA1 and IgA2) isotypes respectively. Antibody herein is meant to include full length antibodies and antibody fragments, and may refer to a natural antibody from any organism, an engineered antibody, or an antibody generated recombinantly for experimental, therapeutic, or other purposes.

Immunoglobulins and antibodies are immunological proteins that bind a specific antigen. In most mammals, including humans and mice, antibodies are constructed from paired heavy and light polypeptide chains. The light and heavy chain variable regions show significant sequence diversity between antibodies, and are responsible for binding a target antigen. Each chain is made up of individual immunoglobulin (Ig) domains, and thus the generic term immunoglobulin is used for such proteins.

By "full length antibody" as used herein is meant the structure that constitutes the natural biological form of an antibody, including variable and constant regions. For example, in most mammals, including humans and mice, the full length antibody of the IgG isotype is a tetramer and consists of two identical pairs of two immunoglobulin chains, each pair having one light and one heavy chain, each light chain comprising immunoglobulin domains VL and CL, and each heavy chain comprising immunoglobulin domains VH, Cγ1, Cγ2, and Cγ3. In some mammals, for example in camels and llamas, IgG antibodies may consist of only two heavy chains, each heavy chain comprising a variable domain attached to the Fc region.

By "immunoglobulin" herein is meant a protein comprising one or more polypeptides substantially encoded by immunoglobulin genes. Immunoglobulins include but are not limited to antibodies (including bispecific antibodies) and Fc fusions. Immunoglobulins may have a number of structural forms, including but not limited to full length antibodies, antibody fragments, and individual immunoglobulin domains Immunoglobulins disclosed herein may be a variety of structures, including, but not limited to antibody fragments, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and fragments of each, respectively.

In one embodiment, an antibody disclosed herein may be an antibody fragment. Specific antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment, which consists of a single variable, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site, (viii) bispecific single chain Fv dimers, and (ix) "diabodies" or "triabodies", multivalent or multispecific fragments constructed by gene fusion. The antibody fragments may be modified. For example, the molecules may be stabilized by the incorporation of disulphide bridges linking the VH and VL domains. Examples of antibody formats and architectures are described in Holliger & Hudson, 2006, Nature Biotechnology 23(9):1126-1136, and Carter 2006, Nature Reviews Immunology 6:343-357 and references cited therein, all expressly incorporated by reference.

In one embodiment, an antibody disclosed herein may be a multispecific antibody, and notably a bispecific antibody, also sometimes referred to as "diabodies". These are antibodies that bind to two (or more) different antigens. Diabodies can be manufactured in a variety of ways known in the art, e.g., prepared chemically or from hybrid hybridomas. In one embodiment, the antibody is a minibody. Minibodies are minimized antibody-like proteins comprising a scFv joined to a CH3 domain. In some cases, the scFv can be joined to the Fc region, and may include some or all of the hinge region. For a description of multispecific antibodies see Holliger & Hudson, 2006, Nature Biotechnology 23(9):1126-1136 and references cited therein, all expressly incorporated by reference.

Delivery of Disclosed Composition

The composition disclosed herein may be delivered to a treatment site in several ways, for example by injection. In some embodiments, the disclosed composition may be delivered by syringe via a needle or tube. In some embodiments, the disclosed composition is placed at a treatment site without a syringe, for example by hand.

Delivery of Therapeutic Agents from Microspheres

In some embodiments a therapeutic agent is released from an encapsulating particle. For example the encapsulating particle may be a microsphere comprised of a biodegradable polymer. In some embodiments, the therapeutic agent is contained within the microsphere, and/or attached to the microsphere. In some embodiments, the microsphere may be delivered directly to a treatment site and in other embodiments the microspheres may be embedded in a biodegradable gel, for example a hydrogel. In some embodiments the microsphere may be comprised of PLGA.

In some embodiments microspheres may be able to release an antibody, such as anti-VEGF. In some embodiments the therapeutic agent may be released from a microsphere—hydrogel systems, and may bind to a molecule, hormone, protein, or peptide produced by a cell. In many embodiments, release of a therapeutic agent or agent from the disclosed composition may reduce the local concentration of a target molecule, hormone, protein, or peptide. In some cases binding of the molecule, hormone, protein or peptide may render it inactive. In some cases the therapeutic agent is an antibody that binds VEGF protein produced by glioma cells.

In some embodiments, for example where the therapeutic agent is anti-VEGF antibody, the amount of soluble VEGF measured by ELISA may be lower in an anti-VEGF treated sample compared to a control sample, for example, empty microspheres in alginate or no hydrogel system at all.

Release Rates

A stable rate may refer to a release rate that varies little over time. A stable release rate, may in some cases be referred to as a controlled release rate, controlled rate, or controlled manner. In most cases, a steady state is achieved when the release rate varies by less than about 20%, 15%, 10% or 5% over the course of about 1 h, 2 h, 3 h, 4 h, 5 h, 6 h, 7 h, 8 h, 9 h, 10 h, 11 h, 12 h, 18 h, 24 h, 1.5 days, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, or 5 weeks. In some embodiments, the stable rate may deteriorate over time. In many cases the release rate may gradually approach zero. In some cases, the release rate may not be steady immediately after the disclosed composition is administered. In these cases, the release rate may have an initial release rate. During this stage, the release rate may be referred to as an initial release rate, and the initial release rate may be more rapid or less rapid than the stable rate, which may be achieved hours or days after the disclosed composition is administered.

Fine tuning of release rates from biodegradable polymers is possible. In some cases, release rates may be modified by altering the extent or amount of cross-linking of a polymer. For example, this may be accomplished by changing cross-linking times for a biodegradable polymer, biodegradable gel or microsphere, for example a chitosan microsphere. Release rates may also be modified through selection of different polymers, for example PLGA polymers. In some cases the use of different endcaps on a polymer may affect release rates, for example ester end-caps may be used instead of acid end groups to increase the time needed for polymer degradation and presumably slower antibody release.

In other embodiments, inherent viscosity (i.v.) of the polymer can be varied. In these cases, polymers with a lower i.v. may degrade more quickly than those with a higher i.v. Release rates can also be tailored by altering the amount of therapeutic agent incorporated, for example by modifying the amount of antibody incorporated into a biodegradable polymer or microsphere. In other embodiments, the antibody can be adsorbed onto a microsphere, for example a chitosan microsphere, rather than incorporating the antibody or therapeutic agent within the microsphere. In another case, the release rate may be altered by modification of the polymer backbone with a bioactive molecule that would provide affinity binding to the therapeutic compound, for example a bioactive molecule able to bind a therapeutic antibody.

In some cases, tethering may be used to control release. In these embodiments, for example, the therapeutic agent may be covalently or non-covalently associated with the polymer backbone. In some cases, the association may be indirect, that is, association may be through another molecule. In these embodiments, a molecule may be covalently attached to the polymer backbone that has affinity for the therapeutic agent, this may help retain the therapeutic agent within the gel or polymer. In some cases, the covalently attached molecule may have affinity for a therapeutic antibody, for example the molecule may be Protein A, which may reversibly bind an Fc portion of a therapeutic antibody. In some case, a hyaluronic acid scaffold with a tethered nogo-66 receptor antibody may be used to promote axonal growth after stroke or spinal cord injury.

Treatment

Treatment or treating of a disease or condition refers to reversing, alleviating, arresting, or ameliorating a disease or at least one of the clinical symptoms of a disease, reducing the risk of acquiring a disease or at least one of the clinical symptoms of a disease, inhibiting the progress of a disease or at least one of the clinical symptoms of the disease or reducing the risk of developing a disease or at least one of the clinical symptoms of a disease. Treating or treatment also refers to inhibiting a disease, either physically, (e.g., stabilization of a discernible symptom), physiologically, (e.g., stabilization of a physical parameter), or both, and to inhibiting at least one physical parameter that may or may not be discernible to the patient. In certain embodiments, treating or treatment refers to delaying the onset of a disease or at least one or more symptoms thereof in a patient who may be exposed to or predisposed to a disease even though that patient does not yet experience or display symptoms of the disease.

A therapeutically effective amount refers to an amount of therapeutic agent that when administered to a subject for treating a disease or a condition, or at least one of the clinical symptoms of a disease or condition, is sufficient to effect such treatment of the disease, condition, or symptom thereof. The therapeutically effective amount may vary depending, for example, on the agent used, the disease and/or symptoms of the disease, severity of the disease and/or symptoms of the disease, the age, weight, and/or health of the patient to be treated, and the judgment of the prescribing physician. An appropriate effective amount in any given agent may be ascertained by those skilled in the art and/or is capable of determination by routine experimentation.

"Therapeutically effective dose" refers to a dose that provides effective treatment of a disease or condition in a patient. A therapeutically effective dose may vary from agent to agent and/or from patient to patient, and may depend upon factors such as the condition of the patient and the route of delivery. A therapeutically effective dose may be determined in accordance with routine pharmacological procedures known to those skilled in the art.

Treatment Sites

A treatment site, as used herein is a location in or on a patient to which the disclosed composition is delivered. A patient, as used herein, refers to a mammal, and in some embodiments a human being. In some cases, the treatment site may be internal or external. In some cases, the treatment site is within the CNS. In some embodiments, the treatment site is a tumor site, either before or after the tumor is resected. In some cases, the treatment site is a tumor that is not resected.

Treatment sites may be locations where growth of cells and tissues is to be controlled. For example, in some cases, such as a tumor site, the disclosed composition is delivered to inhibit growth of epithelial cells into vessels, or to inhibit the growth of cancer cells. In other embodiments, the disclosed composition may be delivered to a location where tissue or cells have been destroyed and new growth is desired.

Therapeutic Action

Where growth of cells and tissues is to be controlled, growth may be decreased or increased. In many cases, treatment of cancer cells with the disclosed composition may be intended to result in decreased proliferation, differentiation, and migration of cancer cells as well as surrounding cells. In some cases, epithelial cells may not form tube structures and/or blood vessels. In some cases, for example where glioma cells may be treated with a biodegradable gel composition, the glioma cells may display decreased crosstalk with endothelial cells. In some cases, the glioma cell's growth is targeted directly and reduced.

In some cases, such as where new growth is desired, treatment with the therapeutic agent may enhance proliferation, differentiation, and migration of target cells and surrounding cells. In some cases, the disclosed composition is used in tissue regeneration. In some cases, the composition is used to enhance the growth of neural cells, such as where a nerve has been severed or damaged.

In some cases, therapeutic agents may bind target cells and/or proteins produced by target cells. For example, in one embodiment an anti-VEGF antibody may be released from the microsphere—hydrogel systems and bind to VEGF (and thereby aid in rendering VEGF inactive) produced by glioma cells. In some cases, therapeutic action may be determined by measuring a target cell and or target protein expressed by the target cell. For example, in one embodiment, the amount of VEGF measured by ELISA is lower in samples treated with an anti-VEGF composition than in control-treated samples (for example, empty microspheres in alginate or no hydrogel system at all).

Therapeutic agents include antibodies that target certain factors and/or receptors. In one embodiment, therapeutic agents may target migratory factors/chemokines and/or their receptors. In one embodiment the therapeutic agent may target C-X-C chemokine receptor type 4 (CXCR-4; fusin; CD184), and inhibit migration signals. CXCR4 may refer to the receptor for CXCL12 chemokine. Other targets involved in metastasis are disclosed. Chemokines and chemokine receptors may also be targeted by the therapeutic agents, for example potential chemokines targeted by therapeutic agents include CCL (1-28) and also CXCL (1-17), and chemokine receptor targets include CXCR(1-7) and CCR (1-10). In many embodiments, the therapeutic agent is an antibody that binds the target.

Therapeutic agents may also target growth factors/cytokines. In some embodiments the therapeutic agent is an antibody that binds to a growth factor in order to diminish its effect, especially on cells surrounding the cell producing the growth factor. For example, therapeutic antibodies may bind TGFs, IGFs, BMPs, VEGFs, PDGFs, EGF, FGFs, HGFs, and/or NGFs. In some embodiments, the growth factor target may be selected from TGF-β 1-3, IGF1 & 2, BMP1-15, VEGF-A, B, C, and D, PDGF-A, B, C, D, EGF, FGF1-23, HGF, NGF. In other embodiments the therapeutic agent may target a cell receptor for a growth factors, including those listed above.

Therapeutic Agent-Containing Particles

In some embodiments, the disclosed composition or therapeutic agent may be encapsulated in a particle. In some embodiments the particle may be a biodegradable particle, for example a sphere. In some embodiments the particle may be a microsphere having at least one measurable dimension less than about 500 µm. In various embodiments, the particle may be comprised of one or more biodegradable polymers, such as alginate, chitosan, hyaluronic acid, collagen, collagen, GAG (glycosaminoglycan), chondroitan sulfate, poly (ethylene glycol) (PEG), gelatin, poly(lactic-co-glycolic acid) (PLGA), polyesters, and combinations thereof, for example collagen/GAG scaffolds, alginate/chitosan composites, and alginate/PEI (polyethylenimine) composites.

EXAMPLES

The following non-limiting examples illustrate various aspects of the disclosure and are not intended to limit its scope, but to illustrate the disclosed compositions, their manufacture, and methods of using the same. These examples are not meant to constrain the present invention to any particular agents, application, mechanism, mode, or theory of operation. It will be apparent to those skilled in the art that many modifications, both to materials and methods, may be practiced without departing from the scope of the disclosure.

Example 1

Engineering of Biopolymer Microspheres

The experiments disclosed here analyzed the engineering of biopolymer microspheres for use in biodegradable carrier gels for providing sustained and localized release of bioactive antibody.

Rationale:

Alginate is a biocompatible, biodegradable natural polysaccharide derived from seaweed that consists of 1,4-linked β-D-mannuronic acid and α-L-guluronic acid. The carboxylic acid groups on the guluronic acid units can be ionically crosslinked with divalent cations such as calcium to form hydrogels. The gentle crosslinking procedure does not damage incorporated bioactive factors. Preliminary results for human IgG release from alginate hydrogels indicate that release occurs rapidly and plateaus off (similar to release of IgG from carboxymethyl cellulose hydrogels). Alginate hydrogels can be 98% water, and retaining bioactive factors in these unmodified hydrogels for sustained delivery can be a challenge.

Incorporation of an antibody into biodegradable chitosan and poly(lactic-co-glycolic acid) (PLGA) microspheres was investigated. These experiments provide substantial control over the rate of release by changing parameters such as microsphere diameter, degree of crosslinking, and polymer concentration, composition, and molecular weight. Antibody-laden microspheres were embedded in alginate hydrogels, serving two purposes: to keep the microspheres localized at the site of interest and to prevent any biofouling of the microspheres, as alginate is a non-fouling material. Biofouling of a release system can be very detrimental as the drug payload is delivered first to the cells that are encapsulating the delivery device and/or must penetrate the cell/matrix encapsulation in order to hit the target tissue. Alginate—microsphere systems are injectable and can conform to the shape and size of the cavity into which they are injected; they are also biodegradable. The antibody was released from the microsphere and diffused out of the alginate to contact surrounding cells.

Experimental Design:

The rate of release of antibody from the following biopolymers was determined: chitosan microspheres, PLGA microspheres, and each of these microsphere types embedded in alginate hydrogels. The polymer conditions were varied. This variation altered the rate of release as shown in Table 1. Human IgG was used as a model therapeutic agent. The rate of release of IgG was measured via protein staining, and the activity of the antibody confirmed via enzyme-linked immunosorbent assays (ELISAs). The two conditions that provided the steadiest release over the course of one month were then tested with encapsulated anti-VEGF antibody, and the anti-VEGF microspheres were also be encapsulated within alginate hydrogels.

Methods: Microsphere Fabrication: Chitosan Microspheres:

Chitosan droplets were produced by one of two separate methods to produce a range of droplet diameters: co-axial capillary flow (diameter ~500 μm) and microfluidic T-junction (diameter ~200 μm). For all methods, 2% w/v chitosan is dissolved in a dilute acetic acid solution and filtered with a 37 μm metal screen. The antibody is then be mixed into the chitosan solution. A syringe pump is used to drip the chitosan/antibody solution from directly above into a beaker that contains an inversion bath (top phase of mineral oil to improve sphericity; and bottom phase of 2M NaOH for phase inversion). After 24 hours in the NaOH, droplets were transferred to a 25 mM genipin solution for amine cross-linking for either 4 or 24 hours. After this time, the particles were lyophilized until dry.

For the capillary device, the droplets were formed between two glass slides sealed together by epoxy. Chitosan will flow in from a 22-gauge needle and into a 100 μl glass capillary tube. The sheath fluid of mineral oil is introduced by a glass capillary and provides the co-axial flow needed to detach chitosan droplets. The oil and chitosan droplets drip directly from the outlet tube into the inversion bath. Preliminary experiments demonstrated that a sheath flow of 100 mL/hr and a droplet flow of 2 mL/hr provided rapid production of 500 μm droplets with narrow polydispersity.

Figure 1:
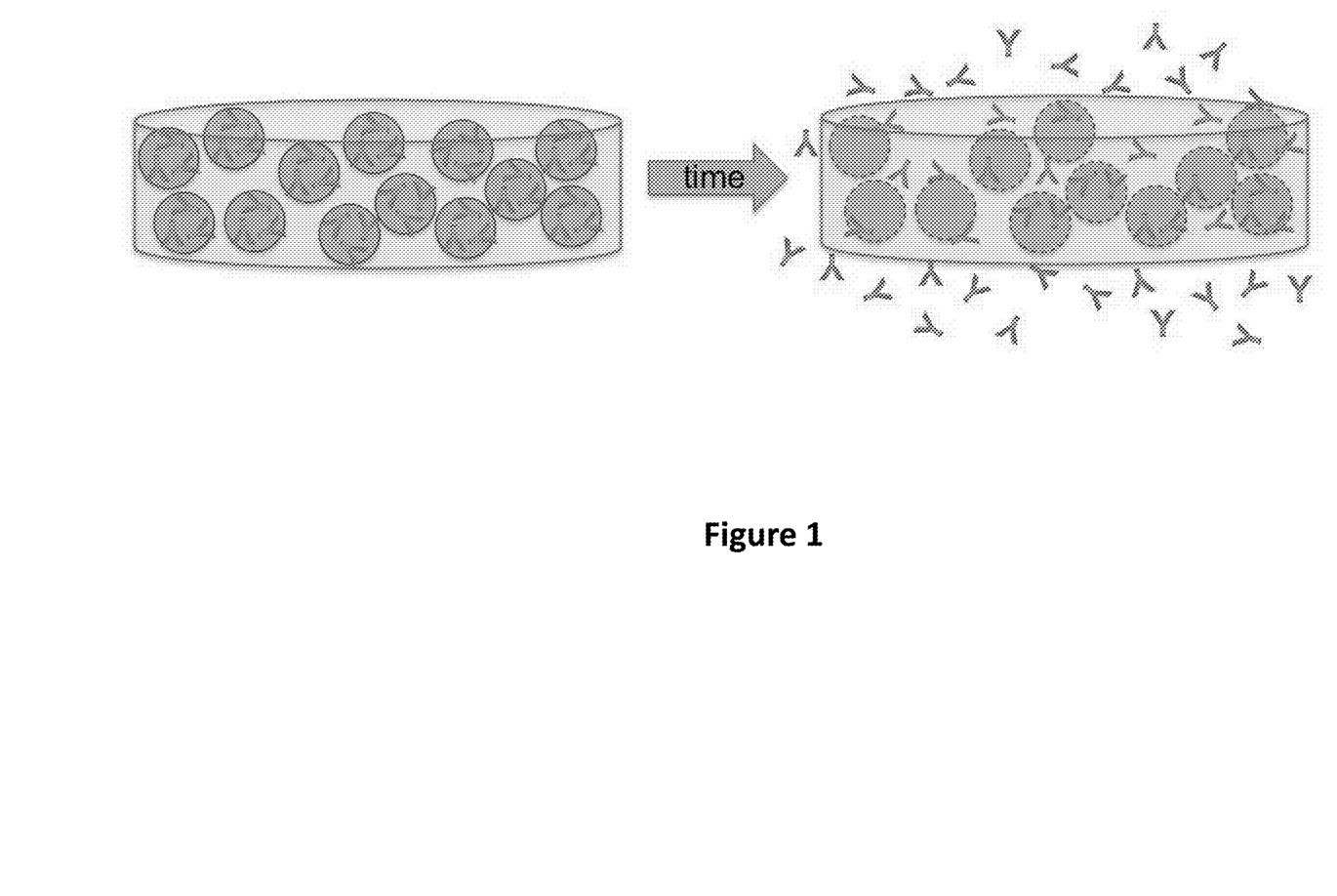
FIG. 1 is a schematic representation of one embodiment of the disclosure. Here, antibody is released, over time, from biopolymer microspheres embedded in a hydrogel.
Figure 2:
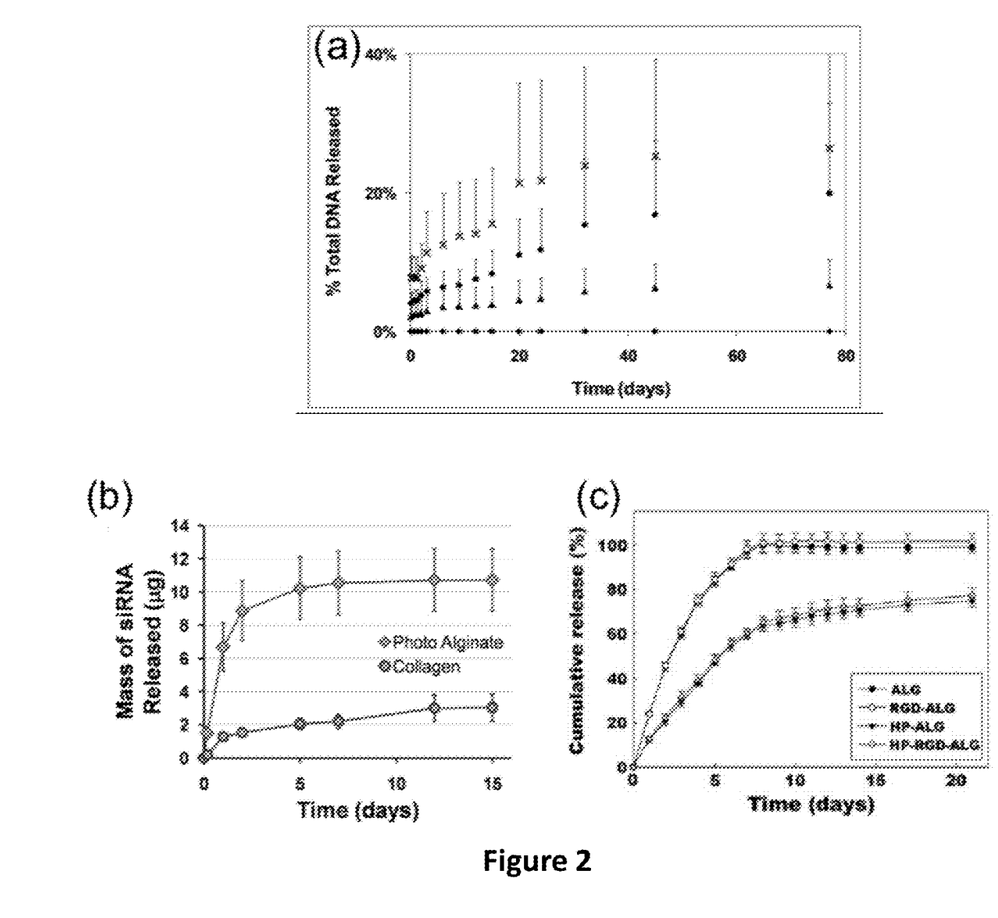
FIG. 2 depicts release profiles of various embodiments of the disclosed composition.
Figure 3:
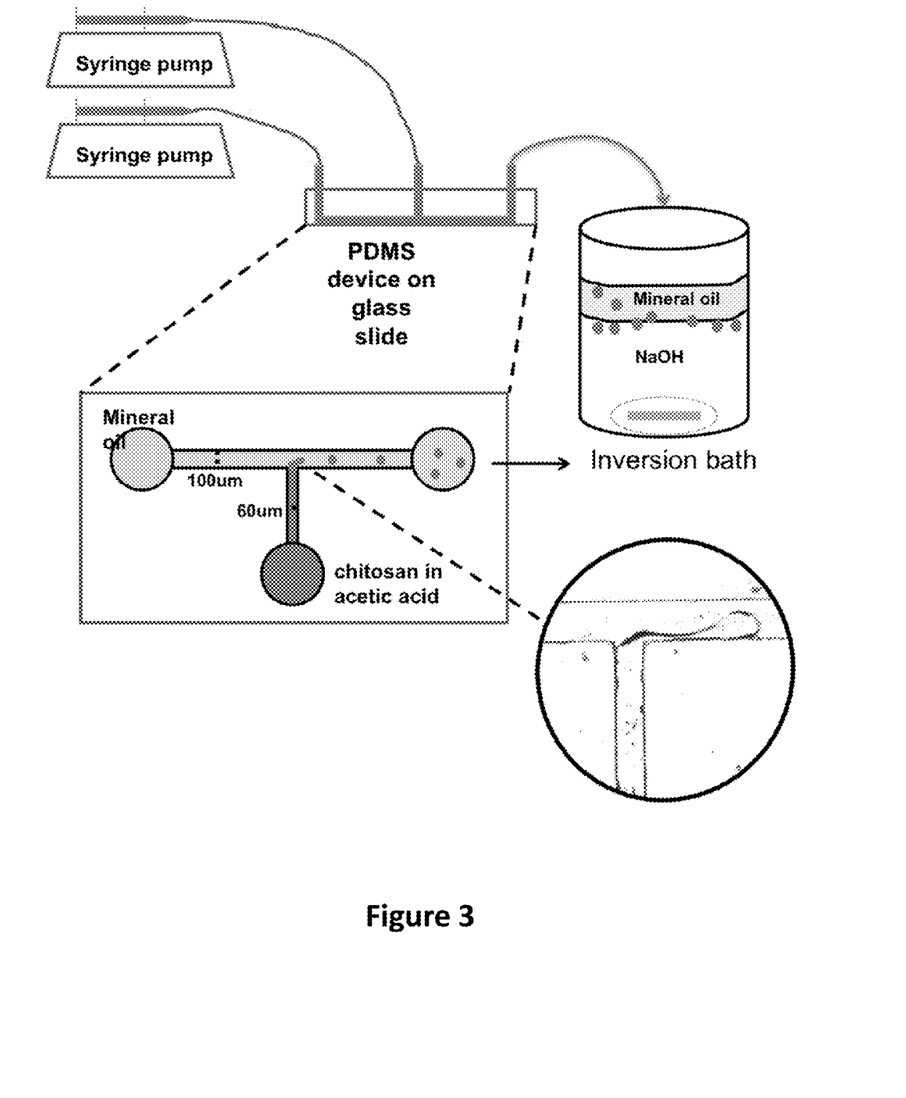
FIG. 3 is a schematic representation of a microfluidic device used for fabrication of small chitosan microspheres.

For the microfluidic device, PDMS (polydimethylsiloxaneis used to create a T-junction pattern. The device and Tygon tubing were silane-coated to improve hydrophobicity and prevent droplet coalescence. Mineral oil flowed from the continuous phase inlet and chitosan solution flowed from the dispersed phase inlet; the outlet flowed into the inversion bath (FIG. 3). Droplet formation can be tuned due to the dominating surface effects. This can be achieved by changing viscosity via addition of sodium dodecyl sulfate or by varying the flow rate and/or weight percent of chitosan solution. Microspheres were produced using an oil flow of 1 μL/min and chitosan flow of 0.2 μL/min.

TABLE 1

Polymer conditions varied

Chitosan Microspheres

| Condition | Particle Diameter (μm) | Crosslinking time (min) |
|---|---|---|
| 1 | 200 | 15 |
| 2 | 200 | 120 |
| 3 | 500 | 15 |
| 4 | 500 | 120 |

PLGA Microspheres

| Condition | Lactic acid to glycolic acid ratio | PVA concentration |
|---|---|---|
| 1 | 85:15 | 0.1% |
| 2 | 85:15 | 1% |
| 3 | 75:25 | 0.1% |
| 4 | 75:25 | 1% |
| 5 | 50:50 | 0.1% |
| 6 | 50:50 | 1% |

Figure 4:
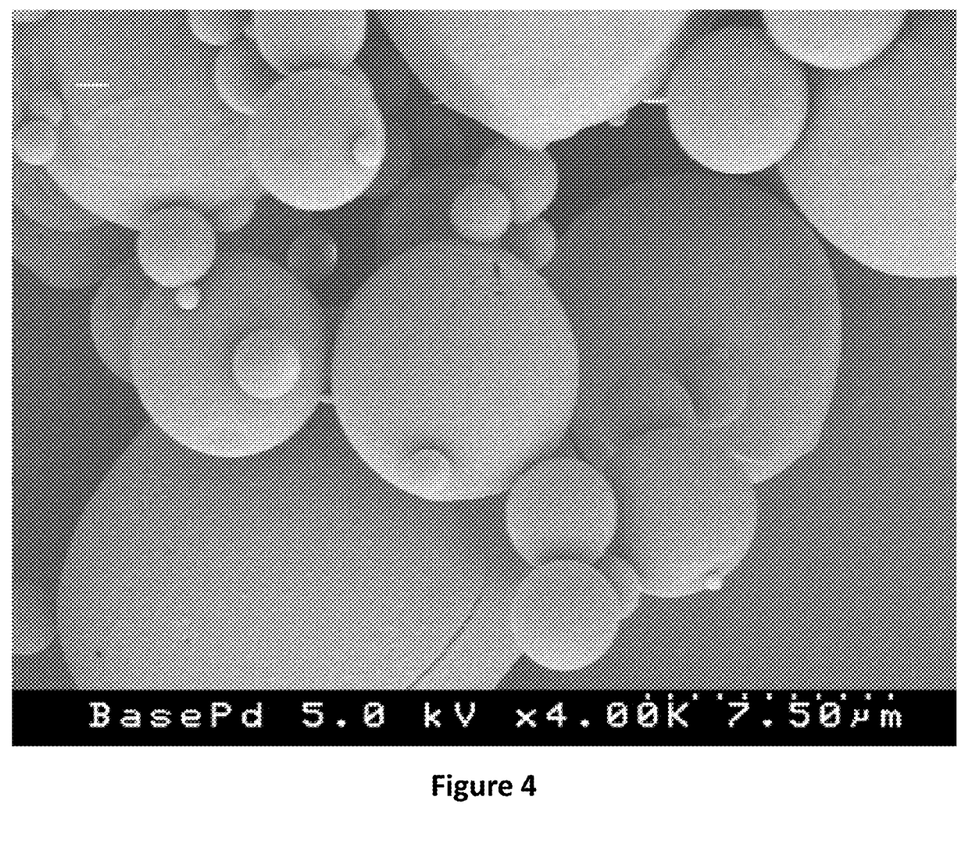
FIG. 4 is a scanning electron micrograph image of PLGA microspheres.

PLGA Microspheres:

Antibody was encapsulated in PLGA microspheres using a water/oil/water double-emulsion technique described at FIG. 4. Antibody was added to the PLGA in ethyl acetate solution and sonicated to form the 1st emulsion. This primary emulsion was then added to an aqueous solution of poly(vinyl alcohol) (PVA) and vortexed to form the 2nd emulsion and stirred in a larger volume of PVA solution to extract the solvent via evaporation. High (1%) and Low (0.1%) concentrations of PVA were used in the secondary emulsion to study its effect on antibody release. Microspheres were rinsed 3× with diH2O prior to lyophilization.

Microsphere Batch Yields and Incorporation Efficiency:

The antibody-laden microsphere batch yields (i.e., mass of microspheres formed/theoretical yield) were determined. The antibody incorporation efficiency for each different polymer microsphere composition is determined by dissolving a known mass of microspheres in a solution of chitosanase (for the chitosan microspheres), or dichloromethane (PLGA) followed by extraction of the antibody into phosphate buffered saline, pH 7.0. The amount of antibody in the solution or extraction is measured using BCA (bicinchoninic acid) protein assay kit (Pierce Technologies). Incorporation efficiency is equal to the quotient of amount of measured antibody and the theoretical incorporated antibody for each microsphere sample.

Release Studies:

Initially all release studies were conducted using human IgG antibody as a model antibody. This provided information about general release characteristics using a less expensive alternative to anti-VEGF antibody. 5 mg antibody-laden microspheres were suspended in 1 ml Dulbecco's Modified Eagle Medium (DMEM). The samples were then incubated at 37° C., with the media replaced every few hours the first day, daily thereafter for the next week, and then every other day for 1-2 months until release was complete. The total amount of released antibody was assayed with BCA or micro-BCA protein assay kit (Pierce), and the bioactivity determined by ELISA (Abcam).

The conditions that provided the steadiest release over time (closest to linear) were used for the remainder of Example 1, where anti-VEGF was examined in place of IgG. For release studies from hydrogels, the anti-VEGF-laden microspheres were mixed into a 2 wt % solution of alginate (purified and sterilized as per Krebs et al., Detection of Biological and Chemical Agents using Differential Mobility Spectrometry (DMS), Technology. *IEEE Sensors Journal,* 5(4), 696-703 (2005)). 100 μl of these mixed solutions was pipetted into a transwell membrane for a 24-well plate, and this membrane submerged into a 0.1 M $CaCl_2$ solution to crosslink. The hydrogels in the transwell membranes were then placed in wells containing 1 ml DMEM at 37° C. and the media replaced as detailed above for the microsphere-only studies. The total amount released and its bioactivity was then assayed as above for the microsphere-only studies.

Conclusion:

Sustained release for at least one month can be obtained by varying the parameters shown in Table 1 and/or using two different types of biopolymer microspheres. Fine tuning is possible with additional crosslinking times for the chitosan microspheres, and with the use of different PLGA polymers (i.e. use of ester end-caps instead of acid end groups may result in longer polymer degradation and presumably slower antibody release, and the inherent viscosity (i.v.) of the polymer can be varied—those with a lower i.v. will degrade more quickly than those with a higher i.v.). Release can also be tailored by altering the amount of antibody incorporated. Also, the antibody can be adsorbed onto the chitosan microspheres rather than incorporated within them if desired to further modify the release rates. Yet another possibility for tailoring release rate in the future could be the modification of the polymer backbone with a bioactive molecule that would provide affinity binding to the antibody. It may also be possible to use a tethering system, for example wherein the therapeutic agent is covalently or non-covalently associated with the polymer backbone. In some cases, a molecule is covalently attached to the polymer backbone that has affinity for the therapeutic agent, this may help retain the therapeutic agent within the gel until the polymer is degraded. In some cases, the covalently attached molecule may have affinity for a therapeutic antibody, for example the molecule may be protein A. In some case, a hyaluronic acid scaffold with a tethered nogo-66 receptor antibody may be used to promote axonal growth after stroke or spinal cord injury.

Example 2

Release of Anti-VEGF from Microspheres

These experiments investigated the ability to deliver anti-VEGF antibody from the microspheres discussed above in Example 1. Specifically, hydrogel systems were studied to determine the amount of soluble VEGF produced by glioma cells, in vitro, over a prolonged period of time.

Rationale:

Although the bioactivity of the released antibody was measured in Example 1 in terms of its ability to still specifically recognize and bind a target protein (via ELISAs), its ability to bind to soluble VEGF produced by glioma cells in vitro was tested in this Example. For this Example, two different human glioma cell lines, U87 and A172, known to secrete VEGF, were examined.

Figure 5:
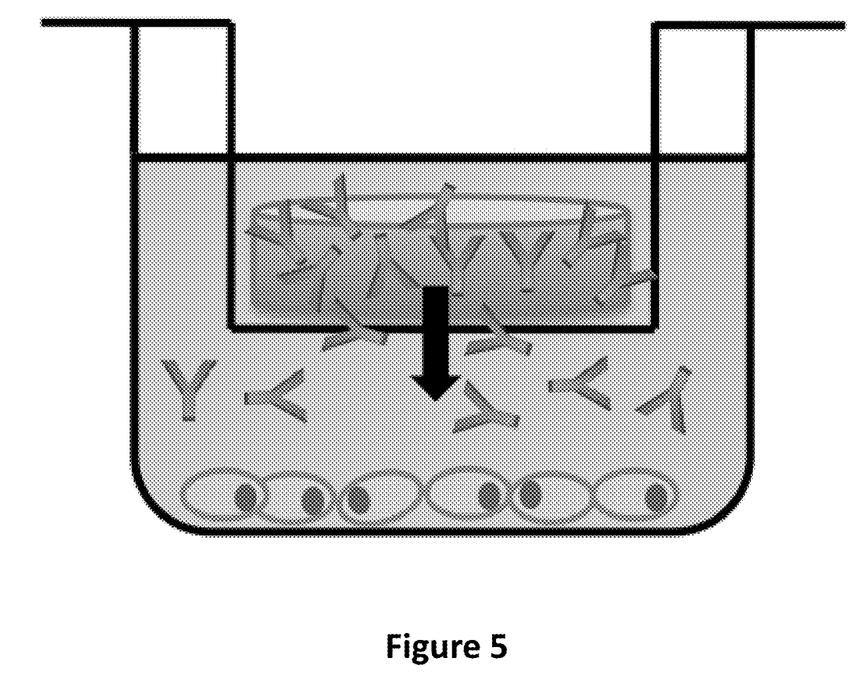
FIG. 5 is a schematic representation of an experiment designed to analyze antibody release from hydrogel into media containing glioma cells.

Experimental Design:

This Example examined the ability of the antibody released from the microsphere—hydrogel system to bind soluble VEGF in a culture of cancer cells. These experiments were accomplished using a transwell assay, with the hydrogel system cultured in a transwell membrane above a monolayer of glioma cells (FIG. 5). Microspheres laden with antibody and empty microspheres were formed, and these microspheres were encapsulated within alginate hydrogels. The amount of soluble VEGF present in the cell culture media was assayed by ELISA, with the hydrogels containing blank microspheres a control to determine the baseline level of VEGF produced by these cells in the presence of the biomaterials; this can also be compared to the amount of VEGF produced by the cells in culture without a hydrogel system present.

Methods: Transwell Assay to Measure Antibody Activity:

U87 and A172 glioma cells were used for these experiments. These cells were plated in 24-well plates at $1.25 \times 10^4$ cells/well. The cells were cultured overnight in a humidified 37° C. incubator with 5% CO2 to allow them to adhere and spread. Antibody-laden microspheres were formed as described in Example 1. The microspheres were encapsulated within calcium-crosslinked alginate also as in Example 1. As a control, empty microspheres were formed and encapsulated into alginate hydrogels. The formed hydrogel system in the transwell membrane was placed into a well over the glioma cells seeded the day before. Every other day for one month, the media in the well was changed, and the spent media saved to assay for the presence of soluble VEGF. The amount of VEGF present was assayed via ELISA.

These experiments establish the ability of anti-VEGF released from a microsphere-hydrogel system to bind to (and thereby render inactive) soluble VEGF produced by glioma cells.

The amount of VEGF measured by ELISA was lower in the anti-VEGF treated samples compared to controls (empty microspheres in alginate or no hydrogel system at all). Soluble VEGF was tested by sampling the media every other day for the duration of the release, which lasted about 1 month. In some cases, especially were VEGF concentrations were low, sampling was reduced to every 3-4 days. Alternatively, more cells were plated into larger wells (while maintaining the same initial cell density).

Example 3

To assess the ability of the delivered anti-VEGF antibody to halt migration and tube formation of endothelial cells cultured with conditioned media from glioma cells.

Rationale:

Cancer cells secrete VEGF which signals endothelial cells to proliferate and migrate towards the cancer cells and form new vasculature, thus aiding in feeding the growing tumor. It is this cross-talk which the present disclosure is directed to. If cancer cells are not able to effectively signal to nearby endothelial progenitor cells, the cancer cells may be unable to recruit the vasculature required to fuel their growth. This is the principle behind antiangiogenic therapies. Thus, this Example uses in vitro assays to assess the ability of the presently disclosed compositions and methods to aid in inhibiting cancer growth. Specifically, this Example investigates a microsphere-hydrogel system to effectively inhibit VEGF and thereby inhibit the ability for endothelial cells in co-culture with glioma cells to behave in an angiogenic manner.

Experimental Design:

Glioma cells and endothelial cells were cultured together, but not in direct contact, using a transwell membrane system. The glioma cells were seeded in a 6-well dish, and endothelial cells seeded on top of a transwell membrane that will be cultured over the glioma cells (37). Every few days, a portion of the media was removed from both the cell culture well and the transmembrane well, and replenished with fresh media. The cells proliferation, viability, expression of VEGF gene (via quantitative PCR (qPCR)), and presence of soluble VEGF (via ELISA) were measured. A Boyden chamber assay was used to examine migration of endothelial cells towards conditioned media from glioma cells. Briefly, the Boyden chamber assay may refer to a cell migration assay, wherein cells are placed on a first side of the membrane in standard cell culture media, and conditioned media or media with drugs or other factor is placed on a second side of the membrane, after which the rate and extent that the cells migrate through the membrane, into the second side, is monitored over time. Finally, an endothelial tube formation assay on collagen gels was used to examine the influence of glioma cells with or without antibody treatment on the tube formation of endothelial cells.

Methods: Co-Culture:

On day 0, U87 and A172 glioma cells were seeded in 6-well dishes at $2.5 \times 10^4$ cells/well, and human umbilical vein endothelial cells (HUVECs) were seeded at the same density in a 6-well transwell membrane with 0.4 µm pores placed in a separate dish. After 48 hours to allow both cell types to adhere and stabilize, the endothelial cells on the transwell were placed over the glioma cells. On this day (day 2), microsphere—hydrogel systems were fabricated and placed into 1 ml DMEM as done in the release studies, described above in Example 1. Every 2-3 days, the media was collected from these hydrogel samples and replenished. The released media was supplemented with FBS to 10%, and supplied to the co-culture system after removing 1 ml media from the co-culture. Controls included released media from hydrogels with empty microspheres, and DMEM not exposed to the hydrogel system. A MTS assay was used as a measure of cell proliferation over time (at 1, 2, 3, and 4 weeks) with each cell type measured independently. At these times, the viability was also tested via LIVE/DEAD assay (Invitrogen). In the MTS assay, each well was rinsed with phosphate buffered saline (PBS), and 1 ml of a 20% Cell-Titer 96 Aqueous One Solution (Promega, Madison, Wis., which contains 3-[4,5-dimethylthiazol-2-yl]-5-[3-carboxymethoxy-phenyl]-2-[4-sulfophenyl]-2H-tetrazolium (MTS-tetrazolium)) was added. The MTS-tetrazolium compound can be metabolized by mitochondria in living cells into a colored formazan product that is soluble in cell culture medium. After incubating at 37° C. for 90 min, 100 ml of each solution was transferred to a 96-well plate and the absorbance was measured at 490 nm using a 96-well plate reader. The expression of the VEGF gene by the cells was measured by qPCR and the spent media assayed for VEGF by ELISA.

Migration Assay:

U87 and A172 cells were seeded in 6-well dishes. After 24 hours, a transwell membrane containing the microsphere-hydrogel system was placed over it. Controls include no hydrogel (cells cultured alone) and hydrogels with empty microspheres. Conditioned media was collected from the well with the glioma cells and stored at −20° C. (saved at 1, 7, 14, 21, and 28 days). A Boyden chamber assay was used to assess the migration of endothelial cells towards the conditioned culture media from glioma cells. HUVECs were seeded at $2.5 \times 10^4$ cells/well in a tissue culture insert with 8 µm pores in a 6-well plate.

Conditioned media from the glioma cells was placed in the well plate under the membrane. After 24 hrs, the membranes were labeled with 8 µM calcein-AM, and the cells migrated to the underside of the membrane detached and their fluorescence measured on a plate reader (42).

Endothelial Tube Formation Assay:

Conditioned media from glioma cells with or without delivered anti-VEGF antibody were collected as for the migration assay, described above. Type I collagen gels at 1.5 mg/ml were formed in the wells of a 24-well plate by incubating a neutralized collagen solution at 37° C. for 45 mins. HUVECs were seeded on the collagen gels at $1 \times 10^5$ cells and, after allowing them to adhere for 30 mins, the media was replaced with the conditioned media from the glioma cells. The cells were photographed every 12 hrs for 3 days. The endothelial tube lengths were analyzed from these photomicrographs using ImageJ software.

Outcomes and Alternative Approaches:

The treatment of glioma cell cultures with antibody-laden hydrogel systems disclosed herein is intended to interfere with cross-talk between glioma cells and endothelial cells. Interfering with cross-talk may aid in decreasing cell proliferation, cell migration, and tube formation by endothelial cells.

In some cases a coating of collagen or matrigel may be required on the tissue culture membrane. In some cases, the migration assays may be performed by fluorescent staining of the cells, or with Giemsa stain.

Example 4

Antibody release from alginate and alginate-chitosan blend hydrogels Alginate and alginate-chitosan hydrogels with encapsulated antibody, in this case IgG, were formed. They were placed into a buffered solution (PBS) and release of the antibody from the hydrogels was measured over time. At pre-determined timepoints, the buffered solution was removed and replaced with fresh solution, and the amount of antibody within the removed solution measured to determine the amount released at that timepoint.

Figure 6:
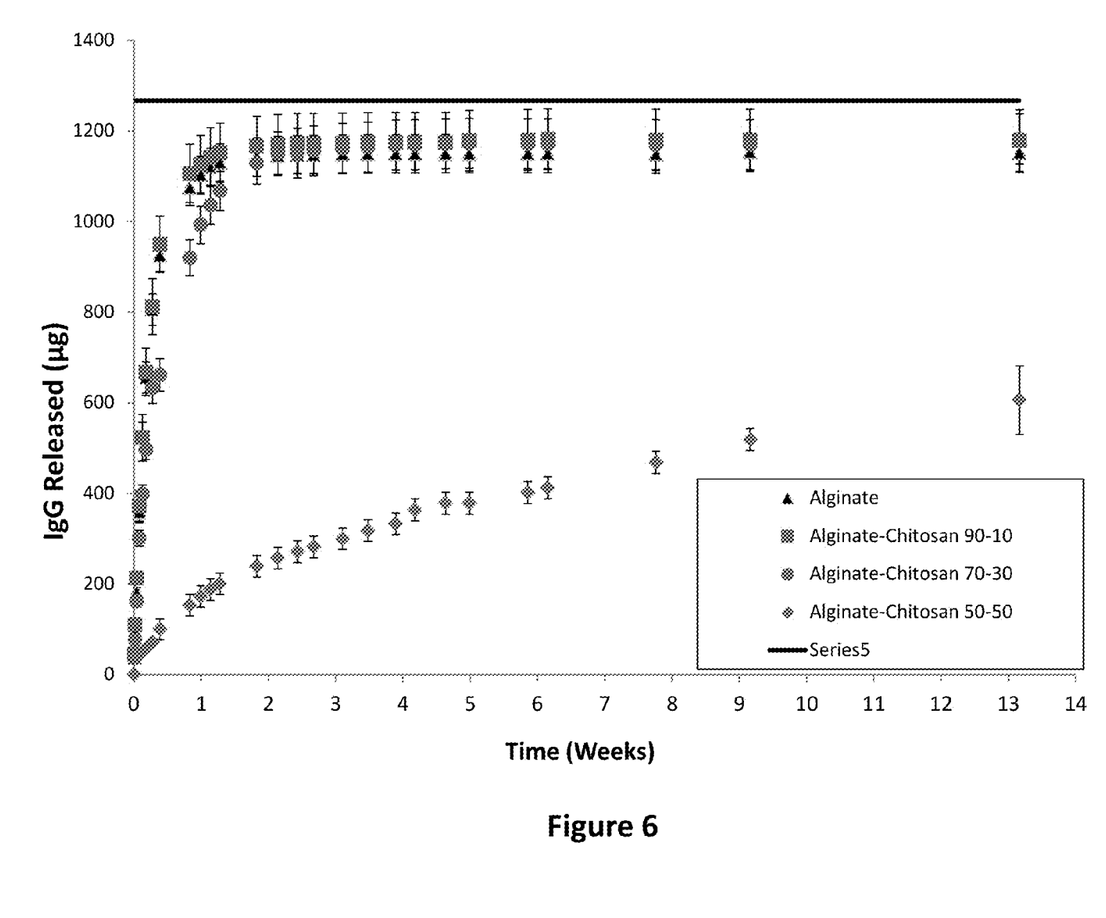
FIG. 6 is a graph of IgG release over time from various embodiments of the disclosed hydrogel, the line at the top of the graph shows the total amount of antibody loaded.

FIG. 6 demonstrates the measurement of the total cumulative amount of antibody released from the various hydrogels over time, with the line near the top of the graph (Series 5) showing the total amount of antibody added.

Materials:

Protanal LF 20/40 food grade alginate was purchased from FMC BioPolymer (Philadelphia, Pa.) and then purified though dialysis (MWCO 3500) and activated charcoal treatment. Protasan UP CL 213, a water soluble chitosan, was purchased from Nova Matrix FMC BioPolymer (Philadelphia, Pa.). Purified Immunoglobin G (IgG) from human plasma was purchased from Athens Research and Technology (Athens, Ga.). Transwell 0.4 µm pore size 12 mm Diameter membranes were purchased from Corning Incorporated (Corning, N.Y.).

Hydrogel Disk Formation:

Alginate disks 2% wt were formed using 2% wt purified alginate solution, calcium sulfate slurry solution (105 mg/mL calcium sulfate in PBS), and antibody solution. The alginate and antibody solutions (or PBS for controls) were loaded into one 3 mL syringe (Beckon Dickson), while 160 µL of the calcium slurry is added to a second 3 mL syringe. For Alginate-Chitosan composite hydrogels, Protasan is loaded into the second syringe with the calcium sulfate slurry. The total volume of biopolymer between the two syringes is always 2 mL, but when making these gels the ratio of alginate to Protasan may change. The two syringes are then connected with a female to female luer lock connector. Mixing is performed by depressing the syringes forcing the total fluid volume back and forth between the syringes 20 times over 5 seconds. Then the contents of the syringes are placed in between two glass plates, which are separated by 2 mm spacers. After 20 minutes the desired diameter of disk can be punched out of the gel sheets.

Alginate Baseline Experiments:

To obtain alginate base line data three ⅜ in diameter alginate disks were created at four different concentrations of IgG: 0 mg/mL, 1.6 mg/mL, 5.0 mg/mL, and 25 mg/mL;

by increasing the amount of spiking solution added. These disks were then placed into 1.5 mL microcentrifuge tubes with 1.0 mL of PBS. Samples were collected by removing the 1.0 mL PBS and placing it in a new microcentrifuge tube to be frozen at −20° C., then replenishing the originale microcentrifuge tube with fresh PBS.

Alginate-Chitosan Composite Experiments:

Alginate-chitosan disks were created with varying concentrations alginate to Protasan ratios by weight: 1 to 0 ("Alginate" in FIG. 6), 1 to 1("Alginate-Chitosan 50-50"), 9 to 1("Alginate-Chitosan 90-10"), and 7 to 3 ("Alginate-Chitosan 70-30"). Six hydrogel disks were created at each ratio with three of each type containing IgG at a concentration 5.0 mg/mL. These disks are then placed into 12 mm diameter Transwell membranes with a 0.4 µm pore size which sit in two 12 well plates. The bottoms of the 12 well plates are then filled with 1.0 mL of PBS. Samples are collected at various times, over 14 about weeks, by removing the PBS from each well and placing it in 1.5 mL microcentrifuge tubes to be frozen in the −20° C. freezer; then placing fresh PBS back in the wells.

Infinite Dilution Experiment:

The gels for this release study were created using 2% wt alginate in PBS, 2% wt Protasan in PBS, 100 mg/mL IgG spiking solution, and Calcium Sulfate slurry solution. Mixing the materials for gel formation was performed within two 3 mL syringes (Beckon Dickson) connected together through a luer lock adaptor. The alginate and 150 µL of spiking solution, or PBS (for the controls), were placed in one syringe while the Protasan and 120 µL of the calcium sulfate slurry solution were placed in the other prior to mixing. The total volume of alginate and Protasan solutions that were mixed into the gels was 1.5 mL. Six of the gels were formed with 1.5 mL of alginate solution (for pure alginate gels) while the other six gels were formed with 1 mL of alginate solution and 0.5 mL of Protasan solution (for a ratio of 2:1 of alginate to Protasan). Three of each type of gel type received the spiking solution while the other three received only PBS solution to serve as controls. Immediately after mixing, the contents were allowed to gel within 70 µm cell strainers (Fisherbrand) for 30 minutes. Then the gel containing cell strainers were placed into 12 one liter beakers containing 500 mL of PBS (+calcium, +magnesium, Hyclone) in which the PBS was stirred continuously by magnetic stir plates. Samples were taken at the given intervals by removing 0.5 mL from the bulk 500 mL of PBS solution and placed into microcentrifuge tubes, which were then frozen in a −20 freezer.

Protein Assay:

The samples from all experiments were thawed out and analyzed using microBCA kits (Pierce) using standards prepared from IgG instead of BSA using the 96 well plate procedure.

All references disclosed herein, whether patent or non-patent, are hereby incorporated by reference as if each was included at its citation, in its entirety.

Although the present disclosure has been described with a certain degree of particularity, it is understood the disclosure has been made by way of example, and changes in detail or structure may be made without departing from the spirit of the disclosure as defined in the appended claims.

I claim:

1. A composition for delivery of a therapeutic agent, the composition comprising:
    a therapeutic agent, comprising an antibody, and
    a biodegradable hydrogel comprising alginate and chitosan, wherein the ratio of alginate:chitosan is from about 70:30 to about 50:50.

2. The composition of claim 1, wherein the therapeutic agent is encapsulated.

3. The composition of claim 2, wherein the therapeutic agent is encapsulated in a microsphere.

4. The composition of claim 3, wherein the microsphere is comprised of a biodegradable polymer selected from the group consisting of chitin and poly(lactic-co-glycolic acid).

5. The composition of claim 1, wherein the ratio of alginate to chitosan in the hydrogel is 50:50.

6. The composition of claim 1, wherein the alginate molecular weight is about 200 kDa.

7. A composition for delivery of a therapeutic agent, the composition comprising:
    a therapeutic agent comprising an antibody,
    a biodegradable polymer microsphere, wherein the therapeutic agent is at least partially contained within the microsphere and/or attached to the microsphere, and
    a hydrogel comprising alginate and chitosan at a ratio of about 70:30 to about 50:50, wherein the microsphere is at least partially contained within the hydrogel.

8. A method of delivering the antibody of claim 1 to a treatment site comprising:
    placing the composition of claim 1 at a treatment site; and thereby delivering the therapeutic antibody.

9. The method of claim 8, wherein the treatment site is a location of a resected tumor.

10. The method of claim 9, wherein the treatment site is inside the blood-brain barrier.

11. The method of claim 8, wherein the placing is done by injecting the therapeutic composition.

12. The method of claim 8, wherein the treatment site is the location of a resected glioma.

13. The method of claim 8, wherein the therapeutic agent is an antibody that inhibits angiogenesis.

* * * * *